United States Patent
Kokkonen et al.

(10) Patent No.: US 10,780,079 B2
(45) Date of Patent: Sep. 22, 2020

(54) VETERINARY METHOD OF ALLEVIATING NOISE AVERSION

(71) Applicant: Orion Corporation, Espoo (FI)

(72) Inventors: Johanna Kokkonen, Espoo (FI); Mira Korpivaara, Littoinen (FI); Nina Sarén, Espoo (FI)

(73) Assignee: ORION CORPORATION, Espoo (FI)

( * ) Notice: Subject to any disclaimer, the term of this patent is extended or adjusted under 35 U.S.C. 154(b) by 0 days.

(21) Appl. No.: 14/679,132

(22) PCT Filed: Oct. 14, 2013

(86) PCT No.: PCT/FI2013/000038
§ 371 (c)(1),
(2) Date: Apr. 6, 2015

(87) PCT Pub. No.: WO2014/060638
PCT Pub. Date: Apr. 24, 2014

(65) Prior Publication Data
US 2015/0258067 A1    Sep. 17, 2015

Related U.S. Application Data

(60) Provisional application No. 61/713,858, filed on Oct. 15, 2012.

(51) Int. Cl.
*A61K 31/4174*    (2006.01)
*A61K 9/00*    (2006.01)
*A61K 9/06*    (2006.01)

(52) U.S. Cl.
CPC .......... *A61K 31/4174* (2013.01); *A61K 9/006* (2013.01); *A61K 9/06* (2013.01)

(58) Field of Classification Search
None
See application file for complete search history.

(56) References Cited

U.S. PATENT DOCUMENTS

| | | |
|---|---|---|
| 4,783,477 A | 11/1988 | Lammintausta et al. |
| 4,910,214 A | 3/1990 | Karjalainen et al. |
| 6,716,867 B1 * | 4/2004 | Aantaa ............... A61K 31/4174 514/396 |
| 2006/0270677 A1 | 11/2006 | Enos et al. |
| 2011/0021588 A1 | 1/2011 | Henwood et al. |
| 2011/0071203 A1 * | 3/2011 | Huhtinen ............. A61K 9/0056 514/396 |

FOREIGN PATENT DOCUMENTS

WO    WO 2010132882 A2 * 11/2010    ............. A61K 9/006

OTHER PUBLICATIONS

Michelazzi, M. et al.: "Effectiveness of L-theanine and behavioral therapy in the treatment of noise phobias in dogs", Journal of Veterinary Behavior: Clinical Applications and Research; vol. 5, No. 1; pp. 34-35; Jan. 2010.
Tyner, C. L. et al.: "Multicenter clinical comparison of sedative and analgesic effects of medetomidine and xylazine in dogs"; Journal of the American Veterinary Medical Association; vol. 211, No. 11; pp. 1413-1417; Dec. 1, 1997.
International Search Report for International Application No. PCT/FI2013/000038, dated Dec. 20, 2013.
Package insert for DEXDOMITOR©, rev. Jun. 2, 2010.
Package insert for SILEO©, rev. Apr. 2016.

* cited by examiner

*Primary Examiner* — Layla Soroush
(74) *Attorney, Agent, or Firm* — Finnegan, Henderson, Farabow, Garrett & Dunner, L.L.P.

(57) ABSTRACT

The invention relates to a method for alleviating noise aversion in animals, particularly dogs, comprising administering to a subject in need thereof an effective amount of dexmedetomidine, medetomidine or a pharmaceutically acceptable salt thereof as the active ingredient. The active ingredient is preferably administered oromucosally, e.g. in the form of an oromucosal gel.

7 Claims, No Drawings

VETERINARY METHOD OF ALLEVIATING NOISE AVERSION

This is a national stage application under § 371 of International Patent Application No. PCT/FI2013/000038, filed Oct. 14, 2013, which claims the benefit of U.S. Provisional Patent Application No. 61/713,858, filed Oct. 15, 2012, both of which are incorporated herein by reference.

TECHNICAL FIELD

The present invention relates to a field of veterinary medicine. In particular, the invention relates to a method of alleviating noise aversion in animals, particularly dogs. The method comprises administering dexmedetomidine or medetomidine or a pharmaceutically acceptable salt thereof to a subject in need of such treatment.

BACKGROUND OF THE INVENTION

Noises aversion is a common problem in companion animals, particularly dogs. It is typically characterized by a fear of loud sounds whereby the dog attempts to avoid or escape from the sound. It is known that at least 20% of dogs suffer from fear of loud noises such as fireworks or thunderstorms. Noise aversion can develop to an excessive fear known as noise phobia. It's an irrational, intense and persistent fear response that can develop at any age and in any dog breed. The symptoms of noise aversion such as phobia may include hiding, urinating, defecating, chewing, drooling, panting, pacing, trembling, shaking and barking. However, the dog owners rarely seek help from veterinarians for treating noise aversion. This may be due to the fact that there are currently no approved veterinary medical products to treat noise aversion and the non-medicinal alternatives have not been shown to be reliably efficient.

Medical therapies suggested in the literature for the treatment of noise aversion in companion animals generally either involve a long period of onset (several weeks) or cause sedation and/or ataxia or have other drawbacks such as human abuse potential. However, most companion animal owners and veterinarians would prefer to treat their animals suffering from noise aversion with a drug which does not promote sedation or ataxia and which is effective within an hour or less of administration.

Moreover, sedation as such does not necessarily eliminate the symptoms of noise aversion. It is known that during the alpha-2 agonist induced sedation animals often remain very sensitive to loud and especially sharp noises. Thus, the noise reactivity remains or is even enhanced despite the sedation.

Thus, there is a need for an effective medical non-sedative treatment of acute noise aversion in companion animals, particularly dogs, having rapid onset of action and sufficiently easy administration such that it could be performed by the pet owner.

Dexmedetomidine and its racemic form medetomidine are alpha-2 adrenoceptor agonists currently used as a sedative and analgesic for dogs and cats. Dexmedetomidine and medetomidine are commercially available as hydrochloride salt in an injectable form only. Dexmedetomidine and medetomidine are currently labeled for veterinary sedation in doses which are 375 µg/m² intravenously or 500 µg/m² intramuscularly of dexmedetomidine hydrochloride, and 750 µg/m² intravenously or 1000 µg/m² intramuscularly of medetomidine hydrochloride.

SUMMARY OF THE INVENTION

It has now been unexpectedly found that noise aversion in animals, particularly dogs, can be effectively alleviated by administering dexmedetomidine or medetomidine or a pharmaceutically acceptable salt thereof in doses that do not produce clinical sedation in subject animals. It has been also found that dexmedetomidine or medetomidine or a pharmaceutically acceptable salt thereof can be conveniently administered for the alleviation of noise aversion by transmucosal administration, particularly in the form of a transmucosal gel adapted for oromucosal administration.

Thus, according to one embodiment of the invention, the present invention provides a method for alleviating noise aversion in animals, particularly dogs, comprising administering to a subject in need thereof an effective amount of dexmedetomidine; medetomidine or a pharmaceutically acceptable salt thereof.

According to another embodiment of the invention, the present invention provides a method for alleviating noise aversion in animals, particularly dogs, comprising administering to a subject in need thereof an effective amount of dexmedetomidine, medetomidine or a pharmaceutically acceptable salt thereof, without producing clinical sedation.

According to another embodiment of the invention, the present invention provides a method for alleviating noise aversion in animals, particularly dogs, comprising administering to a subject in need thereof an effective amount of dexmedetomidine, medetomidine or a pharmaceutically acceptable salt thereof, wherein the subject retains its ability to stand up and walk without signs of ataxia.

According to another embodiment of the invention, the present invention provides a method for alleviating noise aversion in animals, particularly dogs, comprising administering to a subject in need thereof an effective amount of dexmedetomidine, medetomidine or a pharmaceutically acceptable salt thereof, wherein the treated animal remains alert and fully functional such that the animal's ability to eat; move or respond to stimuli is not impaired.

According to another embodiment of the invention, the present invention provides a pharmaceutical veterinary composition in the form of a transmucosal gel comprising dexmedetomidine, medetomidine or a pharmaceutically acceptable salt thereof as an active ingredient.

According to another embodiment of the invention, the present invention provides a method for alleviating noise aversion in animals, particularly dogs, comprising applying effective amount of a composition in a form a transmucosal gel comprising dexmedetomidine, medetomidine or a pharmaceutically acceptable salt thereof as an active ingredient, on the mucosa, particularly oral mucosa, of an animal, particularly a dog.

According to one embodiment of the invention, the present invention provides a veterinary kit comprising a) a composition in the form of a transmucosal gel comprising dexmedetomidine, medetomidine or a pharmaceutically acceptable salt thereof as an active ingredient, b) a package for containing said composition, and c) instructions for administering said composition on the mucosa, particularly oral mucosa, of an animal, particularly a dog, for alleviating noise aversion.

According to one embodiment of the invention, dexmedetomidine, or a pharmaceutically acceptable salt thereof, particularly hydrochloride salt, is used as an active ingredient. According to another embodiment of the invention, medetomidine or a pharmaceutically acceptable salt thereof, particularly hydrochloride salt, is used as an active ingredient.

DETAILED DESCRIPTION OF THE INVENTION

The term "noise aversion", as used herein, refers to increased sensitivity to noise manifested by a fearful and/or phobic response in a subject animal, and includes acute fear associated with noise and noise phobia. Noise aversion is typically invoked by loud noises such as, but not limited to, fireworks, thunderstorms, traffic noise, construction noise and gunshots.

The term "clinical sedation", as used herein, means a state of relaxation characterized by reduced vigilance/alertness and depression of central nervous system functions without total loss of consciousness. Animals appear to be immobilized and sleeping (e.g., dogs are lying on the surface) and do not respond to normal stimulus. Clinical sedation in dogs in a study setting can be defined for instance by posture (lying±rising with difficulty or unable to rise), jaw tone (weakened or very weak), response to noise (no reaction) and ability to perform a particular procedure which requires sedation and restraint.

The present invention relates to a method for alleviating noise aversion in animals, particularly dogs, comprising administering to a subject in need thereof an effective amount of dexmedetomidine, medetomidine or a pharmaceutically acceptable salt thereof. Dexmedetomidine, medetomidine or a pharmaceutically acceptable salt thereof are found to be effective in alleviating noise in doses which do not produce clinical sedation in subject animals. Thus, the treated animals remain alert and fully functional such that the treatment does not impair the animal's ability to eat, move or respond to stimuli (e.g. owner calling the dog).

Dexmedetomidine, medetomidine or a pharmaceutically acceptable salt thereof can be administered to a subject animal suffering from noise aversion e.g. by intravenous or intramuscular route. However, preferably the active ingredient of the invention is administered to a subject animal transmucosally, preferably to oral mucosa of the animal (oromucosally). The active ingredient can be delivered oromucosally using compositions well known in the art, such as patches, wafers, films, solutions or semisolid compositions such as emulsions or gels. In particular, it is preferred to administer dexmedetomidine, medetomidine or a pharmaceutically acceptable salt thereof to a subject animal in the form of a semisolid composition such as an oromucosal gel.

The amount of the active ingredient to be administered is suitably selected such as to provide sufficient noise aversion alleviating effect without undesired signs of clinical sedation. Accordingly; for alleviating noise phobia in animals such as dog, dexmedetomidine or a pharmaceutically acceptable salt thereof, preferably hydrochloride salt, is suitably administered in an amount that produces plasma $C_{max}$ concentration of dexmedetomidine which is from about 0.05 to about 0.8 ng/ml, more typically from about 0.1 to about 0.7 ng/ml, preferably from about 0.15 to about 0.6 ng/ml, more preferably from about 0.2 to about 0.5 ng/ml, for example from about 0.3 to about 0.4 ng/ml. Medetomidine or a pharmaceutically acceptable salt thereof, preferably hydrochloride salt, is suitably administered in an amount that produces plasma $C_{max}$ concentration of medetomidine which is from about 0:1 to about 1.4 ng/ml, preferably from about 0.3 to about 1.2 ng/ml, more preferably from about 0:4 to about 1.0 ng/ml, for example from about 0.5 to about 0.8 ng/ml.

The actual amount of the drug to be administered may depend on numerous factors, such as the species, age and weight of the subject to be treated, the active ingredient used, route of administration and the type of the composition.

For alleviating noise aversion in dog using oromucosal administration; dexmedetomidine or a pharmaceutically acceptable salt thereof, preferably hydrochloride salt, is administered suitably in an amount of about 10 μg/m² to about 200 μm², preferably from about 20 μg/m² to about 180 μg/m², more preferably from about 30 μg/m² to about 150 μg/m², wherein the unit μg/m² refers to micrograms of active agent per squaremeter body surface area of the subject animal. For alleviating noise aversion in dog using oromucosal administration, medetomidine or a pharmaceutically acceptable salt thereof, preferably hydrochloride salt, is administered suitably in an amount of about 20 μg/m² to about 400 μg/m², preferably from about 40 μg/m² to about 360 μg/m², more preferably from about 60 μg/m² to about 300 μg/m², wherein the unit μg/m² is as explained above. Using the oromucosal semisolid gel according to the present invention, dexmedetomidine or a pharmaceutically acceptable salt thereof, preferably hydrochloride salt, is administered preferably in an amount of 50 to 200 μg/m², preferably from 70 μg/m² to 180 μg/m², more preferably from 100 μg/m² to 150 μg/m², and medetomidine or a pharmaceutically acceptable salt thereof, preferably hydrochloride salt, in an amount of 100 to 400 μg/m², preferably from 140 μg/m² to 360 μg/m², more preferably from 200 μg/m² to 300 μg/m².

For alleviating noise aversion in dog using intramuscular injection, dexmedetomidine or a pharmaceutically acceptable salt thereof; preferably hydrochloride salt, is administered generally in an amount of about 1 μg/m² to about 40 μg/m², preferably from about 5 μg/m² to about 30 μg/m², for example from about 10 μg/m² to about 20 μg/m², wherein the unit μg/m² is as explained above. For alleviating noise aversion in dog using intramuscular injection, medetomidine or a pharmaceutically acceptable salt thereof, preferably hydrochloride salt, is administered suitably in an amount of about 2 μg/m² to about 80 μg/m², preferably from about 10 μg/m² to about 60 μg/m², for example from about 20 μg/m² to about 40 μg/m², wherein the unit μg/m² is as explained above.

Weight to body surface area conversion charts for dogs are readily available in veterinary handbooks which are well known to a person skilled in the art.

The semisolid composition useful in method of the invention may be for example, a gel, cream, ointment or paste. Preferred composition is in the form of a gel or emulsion. Gel form is particularly preferred.

Semisolid dosage forms of the invention can be prepared by methods well known in the art. They can be prepared by combining the drug substance with conventional pharmaceutical diluents and carriers commonly used in semisolid formulations.

The particularly suitable semisolid pharmaceutical veterinary composition for use in the present invention is a semisolid gel form adapted for transmucosal administration comprising dexmedetomidine or medetomidine or a pharmaceutically acceptable salt thereof as an active ingredient. The term "semisolid" mean here the mechano-physical state that is flowable under moderate stress. Preferably, the composition is easily syringable, meaning that it can readily be dispensed from a conventional tube of the kind well known for topical formulations or from needleless syringe. The semisolid composition should be viscous enough for being able to remain in the mouth of the animal, however the viscosity should not be so high that the composition could be easily swallowed. Preferably, the semisolid material should have a viscosity from about 500 to about 200,000 mPas, preferably from about 1,000 to about 100,000 mPas, more preferably from about 5,000 to about 50,000 mPas, for example from about 8,000 to about 30,000 mPas. According to one embodiment, the semisolid material has a viscosity from about 3000 mPas to about 50,000 mPas, particularly from about 5,000 mPas to about 20,000 mPas.

The semisolid gel of the present invention has a spreadable consistency upon administration and has been found to be non-irritating even after multiple administrations. Thus, the present composition differs from transmucosal compositions which are in the form of a patch, matrix, film or wafer, which dosage forms may have a drawback of potential irritation of the mucosa.

The gel composition can be applied on any suitable mucosa of an animal including oral, nasal, vaginal and rectal mucosa. In particular, the composition is suitably applied on the oral mucosa of an animal, e.g. buccal, lingual, sublingual or gingival mucosa. For a dog, it is preferably applied to the buccal and/or gingival mucosa, from where the active ingredient is absorbed through the mucous membranes of the oral cavity into the circulation and induces the desired pharmacological effect. The get composition is suitably applied oromucosally in a small volume using a suitable applicator such as a syringe or the like. The composition remains in its application place and is not readily swallowed. The administration of the semisolid dosage is easy and can be performed by the animal owner or handler who is not skilled in parenteral drug administration. The onset of the noise aversion alleviating effect is rapid, and generally starts in dog within 30 minutes from the time application. The duration of the effect is generally from about 120 to about 300 minutes. Thus, the oromucosal route is particularly useful in acute situations such as in the occasions of thunderstorms and fireworks.

Gel, as referred to herein, is a single phase semisolid system consisting of organic macromolecules (gelling agent) uniformly distributed throughout a liquid in such a manner that no apparent boundaries exists between the dispersed macromolecules and the liquid. A veterinary transmucosal composition in the form of a gel has been found to be a particularly suitable for use in the invention.

Gel structure is obtainable by using a suitable gelling agent. The amount of gelling agent is selected such that the resulting gel has the desired theological properties. The gel according to the invention is preferably an aqueous gel (hydrogel), wherein the liquid solvent comprises water. However, the aqueous gel formulation may also comprise suitable water-miscible co-solvents. The active ingredient is uniformly dissolved or dispersed in the gel composition.

Preferably, the transmucosal gel formulation according to the invention comprises dexmedetomidine, medetomidine or a pharmaceutically acceptable salt thereof, a gelling agent, a transmucosal penetration enhancer, water-miscible organic co-solvent and water.

The concentration of dexmedetomidine, medetomidine or a pharmaceutically acceptable salt thereof in the oromucosal composition, e.g. in the semisolid gel composition, is suitably within the range of about 0.001 to about 0.2% (w/w), preferably from about 0.002 to about 0.1% (w/w), suitably from about 0.005 to about 0.05% (w/w), per weight of the composition.

Pharmaceutically acceptable salts of dexmedetomidine and medetomidine can be prepared by known methods. Suitable salts include acid addition salts formed, for example, with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid and the like. Hydrochloride is the preferred salt.

The gelling agent may be any suitable hydrophilic gel forming polymer. Preferably, the gelling agent is selected from cellulose derivatives, polyacrylic acids and polyoxyethylenepolyoxypropylene copolymers. Cellulose derivatives and polyacrylic acids are particularly preferred gelling agents.

Suitable cellulose derivatives for use as gelling agents include cellulose ethers such as hydroxypropyl cellulose, hydroxyethyl cellulose, hydroxyethyl methylcellulose, methylcellulose, hydroxypropyl methylcellulose, hydroxypropyl ethylcellulose, hydroxycellulose and the like. Preferred cellulose ethers include hydroxypropyl cellulose and hydroxyethyl cellulose.

Suitable polyacrylic acids for use as gelling agents include carbomers (also called carboxyvinyl polymers). Carbomers are polyalkenyl polyether cross-linked polymers acrylic acids, typically polyallyl sucrose or polyallyl pentaerythritol cross-linked polymers of acrylic acid. They are available e.g. under the trade name Carbopol in various grades. Aqueous carbomer dispersions are acidic due to free carboxyl groups of the carbomer polymer. Neutralization of the aqueous dispersions of carbomer polymers causes spontaneous thickening through formation of water-soluble salts of polymer resins.

The gel should be viscous enough for being able to remain in the mouth of the animal, however the viscosity should not be so high that the gel could be easily swallowed by the animal.

The gelling agents are generally used in an amount suitable to provide a gel with a viscosity from about 500 to about 200,000 mPas, preferably from about 1,000 to about 100,000 mPas, more preferably from about 5,000 to about 50,000 mPas, for example from about 8,000 toy about 30,000 mPas, measured on a Brookfield Digital Viscometer DV-II, LV-4 (cylindrical spindle), spindle factor 64, 12 rpm, 25° C. According to one embodiment; agents are used in an amount suitable to provide a gel with a viscosity from about 3000 mPas to about 50,000 mPas, particularly from about 5,000 mPas to about 20,000 mPas.

Such suitable viscosity may be obtained by adjusting the amount of gelling agent and/or by adjusting the pH of the composition. This is especially relevant where the gelling agent is a polyacrylic acid such as carbomer as its viscosity is dependent on the pH of the composition.

The amount of the gelling agent depends on the nature of the gelling agent and the desired viscosity. It is preferred that the gel has a spreadable consistency which allows easy oromucosal administration of a small volume of the gel from a syringe or the like. Preferably, the gel composition of the invention is free of bioadhesive components, such as elastomers or the like. Moreover, the gel composition of the invention is preferably not a film-forming type gel composition.

Generally the amount of the gelling agent in the composition of the invention is from about 0.3 to about 40% (w/w), per weight of the composition. In case where the gelling agent is a cellulose derivative, the amount of the gelling agent is typically from about 0.5 to about 40% (w/w), more preferably from about 1 to about 30% (w/w), per weight of the composition. In case where the gelling agent is a polyacrylic acid such as carbomer, the amount of the gelling agent is typically from about 0.3 to about 5.0% (w/w), more preferably from about 0.5 to about 3.0% (w/w), per weight of the composition.

In case where the gelling agent is hydroxypropyl cellulose, it is suitably used in an amount ranging from about 5 to about 40% (w/w), preferably from about 10 to about 25% (w/w), per weight of the composition.

The pH of the composition is suitably within the range of from about 3 to about 9, preferably from about 4 to about 8, more preferably froth about 4.5 to about 7, more preferably from about 5 to about 7, more preferably from about 5.5 to about 6.5, particularly between about 5.8 and 6.2. According to one embodiment, the pH of the composition is within the range of from about 5 to about 6.5. The pH may be adjusted with a suitable basic compound, such as sodium hydroxide, fatty amine or a tertiary amine, or with an acidic compound, such as hydrochloric acid. A gelling agent is typically a slightly acidic material.

Transmucosal penetration enhancers are agents capable of increasing the rate at which the drug permeates through the mucosal membranes and enters the bloodstream. Suitable transmucosal penetration enhancers include for example surfactants, e.g. anionic surfactants such as salts of fatty acids of 5 to 30 carbon atoms, e.g. sodium lauryl sulphate and other sulphate salts of fatty acids; cationic surfactants such as alkylamines of 8 to 22 carbon atoms, e.g. oleylamine; and nonionic surfactants such as polysorbates and poloxamers; aliphatic monohydric alcohols of 8 to 22 carbon atoms such as decanol, lauryl alcohol, myristyl alcohol, palmityl alcohol, linolenyl alcohol and oleyl alcohol; fatty acids of 5 to 30 carbon atoms such as oleic acid; stearic acid, linoleic acid, palmitic acid, myristic acid, lauric acid and capric acid and their esters such as ethyl caprylate, isopropyl myristate, methyl laurate, hexamethylene palmitate, glyceryl monolaurate, polypropylene glycol monolaurate and polyethylene glycol monolaurate; diethyleneglycol monoethyl ether (Transcutol); menthol and other essential oils; salicylic acid and its derivatives; alkyl methyl sulfoxides such as decyl methyl sulfoxide and dimethyl sulfoxide (DMSO); 1-substituted azacycloalkan-2-ones such as 1-dodecylazacyclo-heptan-2-one sold under the trademark AZONE; amides such as octylamide, oleicamide, hexamethylene lauramide, lauric diethanolamide, polyethylene glycol 3-lauramide, N,N-diethyl-m-toluamide and crotamiton; and any other compounds compatible with dexmedetomidine or medetomidine and having transmucosal permeation enhancing activity. One or several of the above transmucosal penetration enhancers can be used. The amount of the transmucosal penetration enhancer in the composition is generally from about 0.1 to about 20% (w/w), preferably from about 0.2 to about 15% (w/w), more preferably from about 0.5 to about 10% (w/w) per weight of the composition, depending on the transmucosal permeation enhancer used.

Preferred transmucosal penetration enhancers are fatty acids of 5 to 30 carbon atoms, particularly isopropyl myristate; sulphate salts of 5 to 30 carbon fatty acids, particularly sodium lauryl sulphate, and DMSO. Sodium lauryl sulphate is particularly preferred.

In case the transmucosal penetration enhancer is sodium lauryl sulphate, it is used in an amount ranging from about 0.1 to about 5% (w/w), preferably from about 0.2 to about 3% (w/w), suitably from about 0.5 to about 2% (w/w), per weight of the composition.

Water-miscible organic cosolvents suitable for use in the gel compositions of present invention include polyalcohols or glycols such as propylene glycol, butylene glycol, ethylene glycol, preferably propylene glycol or $C_2$-$C_4$ alkanols such as ethanol, isopropanol, n-propanol or butanol; or combinations thereof. Preferred are non-volatile organic co-solvents, particularly propylene glycol. The amount of the water-miscible organic co-solvent in the composition is generally from about 5 to about 50% (w/w), preferably from about 10 to about 45% (w/w), more preferably from about 15 to about 40% (w/w), for example from about 20 to about 35% (w/w), per weight of the composition.

The amount of water in the gel composition is generally from about 15 to about 90% (w/w), preferably from about 20 to about 80% (w/w), more preferably from about 30 to about 75% (w/w), for example from about 40 to about 70% (w/w), per weight of the composition.

According to one preferred embodiment, the oromucosal gel formulation comprises per weight of the composition, 0.001 to about 0.2% (w/w) of dexmedetomidine, medetomidine or a pharmaceutically acceptable salt thereof, 0.3-40% (w/w) of a gelling agent; 0.2-15% (w/w) of a transmucosal penetration enhancer; 5-50% (w/w) of a water-miscible organic co-solvent; and 30-80% (w/w) of water.

According to another preferred embodiment, the oromucosal gel formulation comprises per weight of the composition, 0.005 to about 0.1% (w/w) of dexmedetomidine, medetomidine or a pharmaceutically acceptable salt thereof, 1-30% (w/w) of a gelling agent; 0.5-10% (w/w) of a transmucosal penetration enhancer; 5-50% (w/w) of a water-miscible organic co-solvent; and 40-70% (w/w) of water.

According to another preferred embodiment, the oromucosal gel formulation comprises, per weight of the composition, 0.005 to about 0.05% (w/w) of dexmedetomidine, medetomidine or a pharmaceutically acceptable salt thereof, 10-25% (w/w) of hydroxypropyl cellulose; 0.1-5% (w/w) of sodium lauryl sulphate; 15-40% (w/w) of a water-miscible organic co-solvent; and 40-70% (w/w) of water.

The gel composition of the invention can optionally also include other excipients commonly used in the art, for example, preservatives and/or antioxidants such as benzyl alcohol, methyl and propyl parabens, butylhydroxytoluene or butylhydroxyanisole; sweeteners; colouring agents; flavouring agents; buffers; pH adjusting agents; and solubilizers such as glycerol and the like.

The composition of the invention is preferably given to a subject animal oromucosally from a prefilled syringe in a volume ranging from about 0.05 to 5 ml, more preferably from about 0.1 to 2 ml, still more preferably from about 0.2 to 1.5 ml, for example 0.5 ml.

The composition of the invention comprises preferably a colouring agent. For example, a coloured gel can be easily distinguished from saliva following the administration. If the gel product is discharged from the mouth of the animal the owner will be able to note the approximate loss of gel. The owner will also easily note any accidental dosing in case the product comes into contact with his skin.

The composition can be provided in the form of a veterinary kit that comprises composition of the invention, a package for containing said composition, and instructions for administering said composition on the oral mucosa of an animal, particularly dog, for alleviating noise aversion. Preferably, said package is an applicator, e.g. a syringe capable of dosing fixed volumes of the composition of the invention. Syringe is preferably prepared form polymer material, such as HDPE. Suitably, the volume of the syringe ranges from about 0.25 to 6 ml, typically from about 0.5 to 5 ml, more typically from about 1 to 5 ml. For example, composition of the invention can be packaged into 1 ml, 2 ml, 4 ml or 5 ml HDPE syringes.

The invention is further illustrated by the following examples, which are not meant to limit the scope of the invention.

EXAMPLE 1

Oromucosal Gel of Dexmedetomidine HCl

| Ingredient | % (w/w) |
|---|---|
| Dexmedetomidine HCl | 0.01 |
| Hydroxypropyl Cellulose | 15 |
| Propylene Glycol | 30 |
| Sodium Lauryl Sulphate | 1 |
| Sodium Hydroxide (2M) | q.s. |
| Hydrochloric acid, dilute | q.s. |
| Brilliant Blue FCF (E133) | 0.003 |
| Water | 53.987 |

EXAMPLE 2

Oromucosal Gel of Medetomidine HCl

| Ingredient | % (w/w) |
|---|---|
| Medetomidine HCl | 0.02 |
| Hydroxypropyl Cellulose | 15 |
| Propylene Glycol | 30 |
| Sodium Lauryl Sulphate | 1 |
| Sodium Hydroxide (2M) | q.s. |
| Hydrochloric acid, dilute | q.s. |
| Brilliant Blue FCF (E133) | 0.003 |
| Water | 53.977 |

The gel formulations of Example 1 and 2 were prepared by adding propylene glycol, colouring agent, sodium lauryl sulphate and water in a vessel. The mixture was stirred until it was miscible and homogenous. The mixture was warmed to 50° C. Hydroxypropyl cellulose was slowly added under stirring. The gel was cooled to room temperature under gentle stirring and drug substance was added under stirring. pH of the composition was adjusted to 6.0 by dropwise addition of HCl solution. Clear gel was obtained after standing. Gel was packaged into 4 ml HDPE syringes.

EXAMPLE 3

The effect of oromucosal dexmedetomidine gel was studied in dogs that were known to suffer from acute noise aversion due to New Year's Eve fireworks. Twelve dogs of diverse breeds received oromucosal dexmedetomidine gel (group DEX) of Example 1 and twelve dogs of received placebo gel which did not contain dexmedetomidine. The study was double-blinded. The gel was administered to buccal/gingival mucosa of each dog with a syringe using a dose of 125 µg/m² of dexmedetomidine. Redosing up to 5 times was allowed if needed (as soon as signs of noise aversion reappeared) but with minimum time of 2 hours between the dosings. The study was undertaken during New Year's Eve at each dog's home. Efficacy was monitored using owner assessment of the effect of the treatment to dog's signs of noise aversion elicited by fireworks compared to previous years (no effect, some effect or good effect). The results are shown in Table 1.

TABLE 1

Owner assessment of the overall success of the effect of the treatment to dog's signs of noise aversion compared to previous years

| | DEX 125 µg/m² | Placebo |
|---|---|---|
| Response | n (%) | n (%) |
| Overall success* | 8 (66.7) | 3 (25.0) |

*Overall success = dogs scoring, "good effect" without any signs of decreased alertness/sedation

The invention claimed is:

1. A method for alleviating noise aversion in a dog without producing clinical sedation, comprising administering to the dog in need thereof a noise-aversion alleviating amount of dexmedetomidine or a pharmaceutically acceptable salt thereof that does not produce clinical sedation, wherein the amount of dexmedetomidine or a pharmaceutically acceptable salt thereof ranges from 100 µg/m² to 150 µg/m², wherein dexmedetomidine or a pharmaceutically acceptable salt thereof is administered oromucosally in the form of a semisolid oromucosal gel.

2. The method according to claim 1, wherein the semisolid oromucosal gel comprises, per weight of the composition, 0.001-0.2% (w/w) of dexmedetomidine or a pharmaceutically acceptable salt thereof; 1-40% (w/w) of a gelling agent; 0.2-10% (w/w) of a transmucosal penetration enhancer; 5-50% (w/w) of a water-miscible organic co-solvent; and 30-80% (w/w) of water.

3. The method according to claim 1, wherein the plasma $C_{max}$ value of dexmedetomidine in the dog is from about 0.05 ng/ml to about 0.8 ng/ml.

4. The method according to claim 1, wherein the plasma $C_{max}$ value of dexmedetomidine in the dog is from about 0.15 ng/ml to about 0.6 ng/ml.

5. The method according to claim 1, wherein the plasma $C_{max}$ value of dexmedetomidine in the dog is from about 0.2 ng/ml to about 0.5 ng/ml.

6. The method according to claim 1, wherein the dog retains its ability to stand up and walk without signs of ataxia.

7. The method according to claim 1, wherein the dog suffers from noise phobia.

* * * * *